United States Patent
Wang et al.

(10) Patent No.: US 9,784,673 B2
(45) Date of Patent: Oct. 10, 2017

(54) LASER SPECTROSCOPIC SENSOR USING ORBITAL ANGULAR MOMENTUM

(71) Applicant: NEC Laboratories America, Inc., Princeton, NJ (US)

(72) Inventors: Ting Wang, West Windsor, NJ (US); Yi Weng, Lafayette, LA (US)

(73) Assignee: NEC Corporation, Tokyo (JP)

( * ) Notice: Subject to any disclaimer, the term of this patent is extended or adjusted under 35 U.S.C. 154(b) by 42 days.

(21) Appl. No.: 14/842,589

(22) Filed: Sep. 1, 2015

(65) Prior Publication Data
US 2016/0109361 A1 Apr. 21, 2016

Related U.S. Application Data

(60) Provisional application No. 62/064,535, filed on Oct. 16, 2014.

(51) Int. Cl.
| | | |
|---|---|---|
| G01N 21/00 | (2006.01) | |
| G01N 21/3504 | (2014.01) | |
| G01N 21/27 | (2006.01) | |
| G01N 21/21 | (2006.01) | |

(52) U.S. Cl.
CPC ......... *G01N 21/3504* (2013.01); *G01N 21/21* (2013.01); *G01N 21/27* (2013.01); *G01N 2201/06113* (2013.01)

(58) Field of Classification Search
CPC .... G01N 21/3504; G01N 21/27; G01N 21/59; G01N 233/49; G01N 21/65; G01N 21/64; G01N 21/75; A61B 5/00; G01J 4/04; C12M 1/40; G01L 1/24; G01B 11/26
See application file for complete search history.

(56) References Cited

U.S. PATENT DOCUMENTS

| | | | |
|---|---|---|---|
| 7,701,381 B2 | 4/2010 | Schmitt et al. | |
| 8,396,371 B2 | 3/2013 | Murshid et al. | |
| 2012/0288925 A1* | 11/2012 | Wang | G02B 21/32 435/287.2 |
| 2013/0235744 A1 | 9/2013 | Chen et al. | |
| 2014/0098359 A1* | 4/2014 | Gross | A61M 1/367 356/36 |
| 2015/0260650 A1* | 9/2015 | Ashrafi | G01N 21/17 702/25 |

OTHER PUBLICATIONS

N. Uribe-Patarroyo et al, "Object Identification Using Correlated Orbital Angular Momentum States," Physical Review Letters, Jan. 25, 2013, pp. 043601-1-043601-5, PRL 110.

I. Djordjevic, "Deep-space and near-Earth optical communications by coded orbital angular momentum (OAM) modulation," Opt. Express, Jul. 18, 2011, pp. 14277-14289, vol. 19, Issue 15.

J. Wang et al., "Terabit free-space data transmission employing orbital angular momentum multiplexing," Nature Photonics, Jun. 24, 2012, pp. 488-496, vol. 6.

* cited by examiner

*Primary Examiner* — Jamil Ahmed
(74) *Attorney, Agent, or Firm* — Joseph Kolodka

(57) ABSTRACT

A method and system for optical angular momentum (OAM) spectroscopy includes generating a beam of light having a single OAM mode. A first spectrum of the beam of light is detected and the beam of light is passed through a gas to attenuate the beam of light in accordance with a presence and concentration of a respective gas. A second spectrum the beam of light is coherently detected and a difference between the first and second spectrum for the beam of light is analyzed to determine the presence and concentration of the respective gas.

14 Claims, 5 Drawing Sheets

US 9,784,673 B2

LASER SPECTROSCOPIC SENSOR USING ORBITAL ANGULAR MOMENTUM

RELATED APPLICATION INFORMATION

This application claims priority to provisional application 62/064,535, filed Oct. 16, 2014, the contents thereof being incorporated herein by reference.

BACKGROUND OF THE INVENTION

Mid-infrared (MIR) laser spectroscopic sensors have the ability to detect and monitor trace-gas molecules. Such sensors use absorption spectroscopy to measure the concentration of gas molecules. MIR may be defined as wavelengths that fall within a range of about 3μ to about 30 μm, while near IR is generally considered to be in the range of about 0.8 μm and about 3 μm and far IR is generally considered to be in the range of 30 μm to about 300 μm. Many trace gas molecules have their fundamental rotational-vibrational absorption bands, as well as the strongest vibrational bands, occur within the MIR range, with absorption signals several orders of magnitude stronger than those apparent in the near IR range.

One problem for conventional MIR gas sensing is that they are capable of capturing only one spatial component of the field vectors (or projection). There are still properties of light that are not yet fully utilized for such sensors. Current methods focus on wavelength and amplitude.

Another key problem of MIR laser spectroscopic sensors is that they cannot fill a need for high sensitivity and high selectivity simultaneously. Each gas has a unique absorption line pattern, which allows the laser-based sensor to detect its presence. In practice, however, most gases are mixtures of different compounds, which means a series of lines will most often represent a combination of different gases within one absorption spectrum. For example, environmental monitoring often measures a combination of CO, $CO_2$, $CH_4$, $CH_2O$, $C_2HF_5$, $N_2O$ and $NO_2$, while gas pipelines usually contain a mixture of HCl, $CO_2$, $CH_4$, CO, $NO_x$, $CH_2O$. In medical uses, gases may include NO, CO, $NH_3$, $C_2H_6$, $H_2S$, $H_2O_2$, etc. Some of these gases have a very short lifetime and extremely low concentration in chemical reaction processes, such that detecting them with high sensitivity, accuracy, and selectivity is difficult for conventional spectroscopic techniques.

One significant limitation for trace-gas sensors is limited wavelength range. No laser can provide a sufficiently broad wavelength range to separate the absorption lines for different gases when combined together. Conventional techniques use sophisticated calibration procedures to assure satisfactory accuracy in multiple-gas detection, making such approaches prohibitively time consuming.

Other approaches to trace gas detection include electromechanical sensors, which measure an amount of current that corresponds to how much gas is oxidized at an electrode, and semiconductor detectors, which detect gas concentration from the decrease in dioxide electrical resistance. In both cases, direct exposure of the sensor to the gas is needed. Holographic gas sensors use light reflection to detect changes in a polymer film matrix that contains a hologram, and a change in gas composition can generate a colorful reflection indicating the presence of a gas molecule, but it needs illumination sources such as white light or lasers. Nuclear magnetic resonance is highly accurate, but needs a highly purified substance and a relatively long timescale. In addition, none of these technologies are able to distinguish between different gas isotopes, preventing them from being used in advanced gas exploration or biomedical applications.

BRIEF SUMMARY OF THE INVENTION

A method for optical angular momentum (OAM) spectroscopy includes generating a beam of light having a single OAM mode. A first spectrum of the beam of light is detected and the beam of light is passed through a gas to attenuate the beam of light in accordance with a presence and concentration of a respective gas. A second spectrum the beam of light is coherently detected and a difference between the first and second spectrum for the beam of light is analyzed to determine the presence and concentration of the respective gas.

An optical angular momentum (OAM) spectroscopy sensor includes a laser. An OAM converter configured to impose an OAM mode on an output of the laser and produce an OAM beam. A first OAM receiver is configured to detect a first spectrum of the OAM beam from the OAM converter. A gas cavity containing a mixture comprising one or more component gases is configured to attenuate the OAM beam in accordance with a presence and concentration of a respective gas. A second OAM receiver is configured to coherently detect a second spectrum of the OAM beam after the OAM beam has passed through the gas cavity. A processor is configured to analyze a difference between the first and second spectrum for the beam of light to determine the presence and concentration of the respective gas.

DETAILED DESCRIPTION

Figure 1:
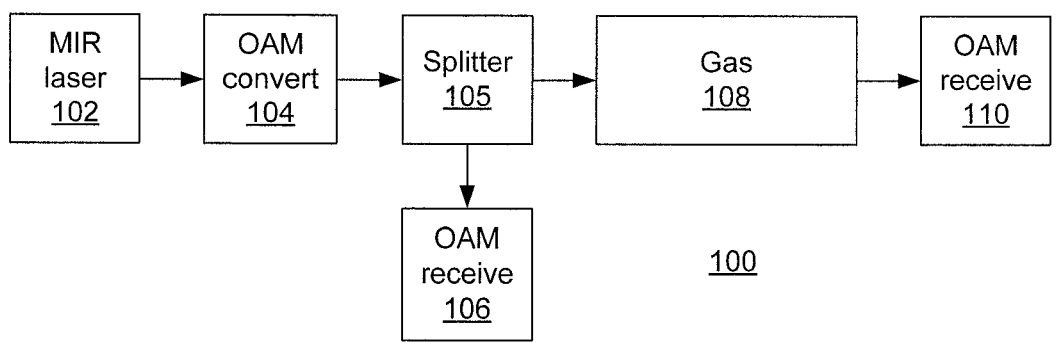
FIG. 1 is a block diagram of an optical angular momentum spectroscopy system in accordance with the present principles.

The present embodiments provide a high-performance, cost-effective, networked trace-gas sensor. In particular, the present embodiments employ the orbital angular momentum (OAM) of light, which provides a measurement that is orthogonal to conventional measurements such as wavelength, phase, amplitude, and polarization, thereby improving sensitivity and extracting more information from gas molecules in contrast to single-mode approaches.

OAM is linked to the spatial distribution of the electric field of light and provides parallel channels, each being an independent orthogonal spatial mode, making it appropriate for the detection of broad-band absorbers and multiple absorption lines. The alteration of any single OAM state in free-space can be detected in a manner similar to signals in multi-mode fibers (MMFs), where each light beam with OAM serves as a carrier of information, with both spatial and polarization degrees of freedom. The monitored gas will alter the OAM states in very different ways due to different polarization and modal properties, such as effective and group indices, dispersion, and effective area. Theoretically, when using N OAM beams to carry different modes, 2N types of gas can be detected simultaneously, and N can be an arbitrarily high number. Moreover, two or more different OAM modes can be used to perform error correction on a single gas, thus providing higher spectral resolution and faster response time.

The strongest interaction between electromagnetic radiation and chemical structures is via dipole interactions, as the dipole moment operator has inversion symmetry across the nucleus of an atom. The dipole moment of the molecule changes as a result of absorption spectroscopy, moving to different energy state. The physical process of photon absorption involves two kinds of angular momentum, including the electron spin angular momentum (SAM) and the electron OAM. When free electrons have OAM, their eigenstates are described by Bessel functions and an arbitrary waveform can be obtained by a superpositions of those eigenfunctions. The probability of a particular molecule absorbing a photon is determined by an orbital momentum selection rule of atomic transitions and electron OAM.

In that sense, the absorption integral is zero if two electron wave functions have the same parity, but non-zero if the electrons have different parity. As a result, the angular momentum has a significant role in the interaction of specific molecules. Heavier molecules may have more SAM-OAM coupling while conserving total angular momentum. There are different absorption integrals for diatomic and linear polyatomic molecules as opposed to non-linear polyatomic molecules. Thus, using specific OAM modes allows the transfer of information encoded in the spatial degrees of freedom of an input light to degrees of freedom within the quantum variables of an atomic ensemble. The changes to those transitions are restricted by the conservation of overall angular momentum to occupy particular angular momentum quantum states.

Referring now to FIG. 1, an exemplary experimental sensor arrangement 100 is shown. An MIR laser 102 is used to generate one or more beams of laser light having a wavelength in the MIR range. The one or more beams are converted to OAM beams having specified angular momentum values at OAM converter 104. The OAM converter 104 may include any appropriate device for producing OAM modes including, e.g., free-space mode conversion using phase plates or hologram plates. An optical splitter 105 splits each beam into two components, one feeding directly to an OAM receiver 106 and the other feeding to a chamber 108 of the gas to be analyzed. Ideally, the gas 108 has its temperature and pressure closely controlled. After passing through the gas 108, a second OAM receiver 110 collects the beams.

It is specifically contemplated that the second receiver 110 is a coherent receiver that uses multiple-input multiple-output (MIMO) and equalization techniques to increase the sensitivity of the detecting system. This moves the complexity of measuring OAM signals from the optical domain to the digital domain.

The OAM beams received by the first OAM receiver 106 and the second OAM receiver 110 are compared to determine how the respective beams were affected by passing through the gas. It should be noted that other spectroscopic measurements may be made simultaneously using, e.g., conventional measurement technologies. The sensor of FIG. 1 uses absorption spectroscopy to measure the concentration of gas molecules, as the laser frequency is tuned to the absorption line of the sample gas 108. When the light passes through the sample gas, it is attenuated and the absorption is spectrally matched with the output wavelength of the laser 102. The light power at the receiver can be approximated by:

$$I=I_0(1-\alpha(v))$$

where $I_0$ is the intensity of the incident light, I is the intensity of the transmitted light, and $\alpha(v)$ is the absorbance of power at the frequency v. At the second receiver 110, a band-pass filter such as a lock-in amplifier may be added to reject noise and thus enhance system sensitivity. A second-harmonic profile is used because it is most similar to the direct absorption profile with signal peak located at the center of the transition spectrum.

Figure 2:
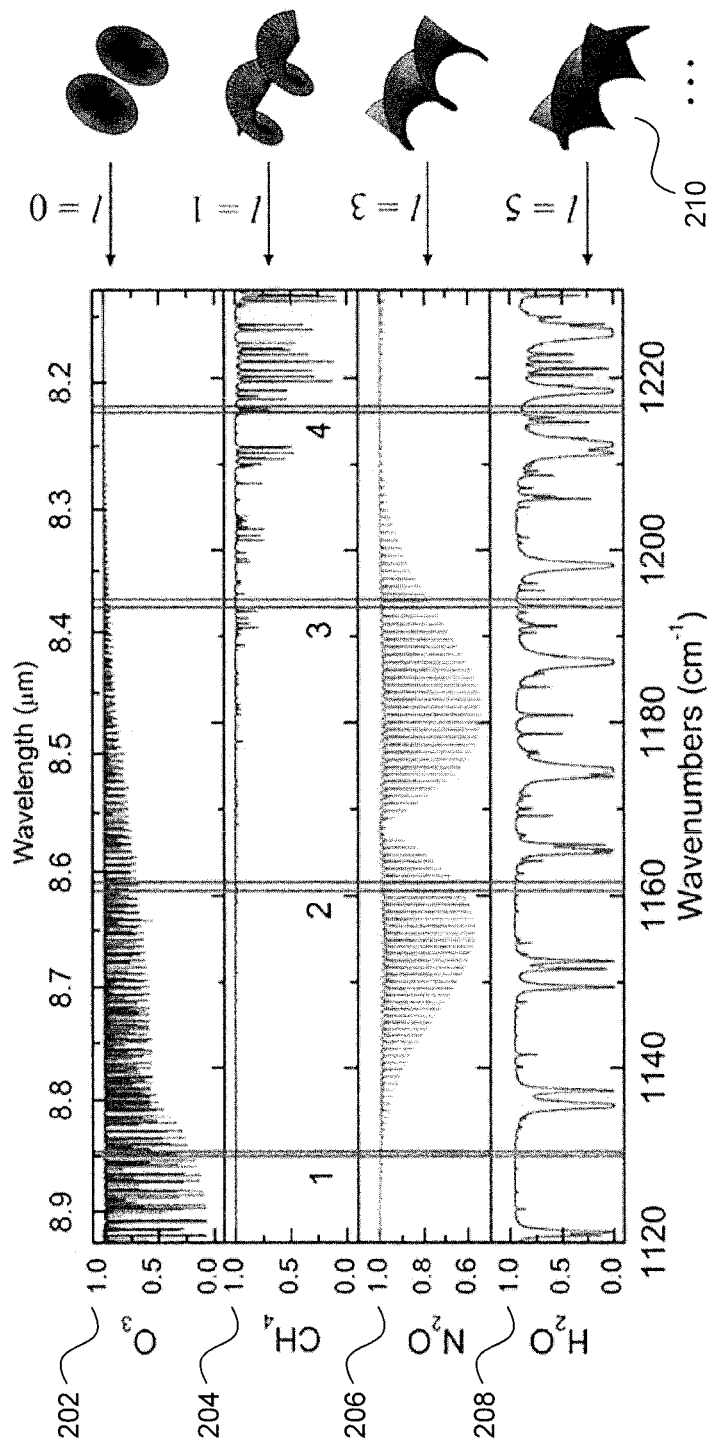
FIG. 2 is a diagram of orbital angular momentum spectroscopy signals in accordance with the present principles.

Referring now to FIG. 2, a diagram of the spectral responses of four different OAM beams is shown. The gases are mixed together in gas 108, which means a series of mixing lines representing different types of gases will be detected within one absorption spectrum. Since OAM is linked to the spatial distribution of the electric field, the additional degree of freedom provided by using both OAM and polarization processing can increase the overall number of parallel channels, with each independent channel on an orthogonal spatial mode. In this case, spectrum 202 detects ozone using a beam having an OAM of zero, spectrum 204 detects methane using a beam having an OAM of 1, spectrum 206 detects nitrous oxide using a beam having an OAM of 3, and spectrum 208 detects water using a beam having an OAM of 5. In each case, the spectral absorption pattern shown is distinctive of the respective gas. For each spectrum, a diagram 210 of the spatial distribution of the electric field of the beam is shown.

It should be noted that, as with other forms of absorption spectroscopy, each gas molecule will produce a distinctive pattern. By matching the detected signal to an expected pattern for the gas in question, the presence and relative concentration can be determined based on how intensely the beam is attenuated at the predicted absorption lines. Orbital mode rotation may be employed to study the OAM imbalance within a sample using a balanced photodiode bridge and coherent detection. The OAM emerges as the singularities of a wave function described by $e^{il\phi}$, where l is the angular momentum quantum state number and $\phi$ is the azimuthal angle of a beam cross section. The angular momentum quantum state number counts the number of optical phase rotations present within the optical wave-front in a single loop around a vortex core. A holographic pitch-fork grating with a spatial light modulator produces diffracted Laguerre-Gauss light with OAM modes l=0, +1, +2, . . . , +N, where N is an integer. The grating may be flipped to produce OAM modes l=0, −1, −2, . . . , −N. The interaction between the OAM beams with e samples then rotates the lobed structure due to OAM birefringence (a mode-dependent difference in index of refraction) and, through a coherent detection of the captured field, the whole spiral spectrum, including both amplitude and phase of a spatial light beam, can be fully retrieved. The difference in absorption for different gas molecules caused by switching between l=+N and l=−N beams can thereby be measured.

Figure 3:
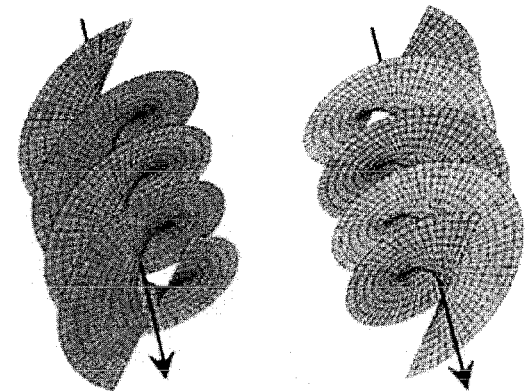
FIG. 3 is a diagram of multiple orbital angular momentum spectroscopy signals being used to attain super resolution in accordance with the present principles.
Figure 3:
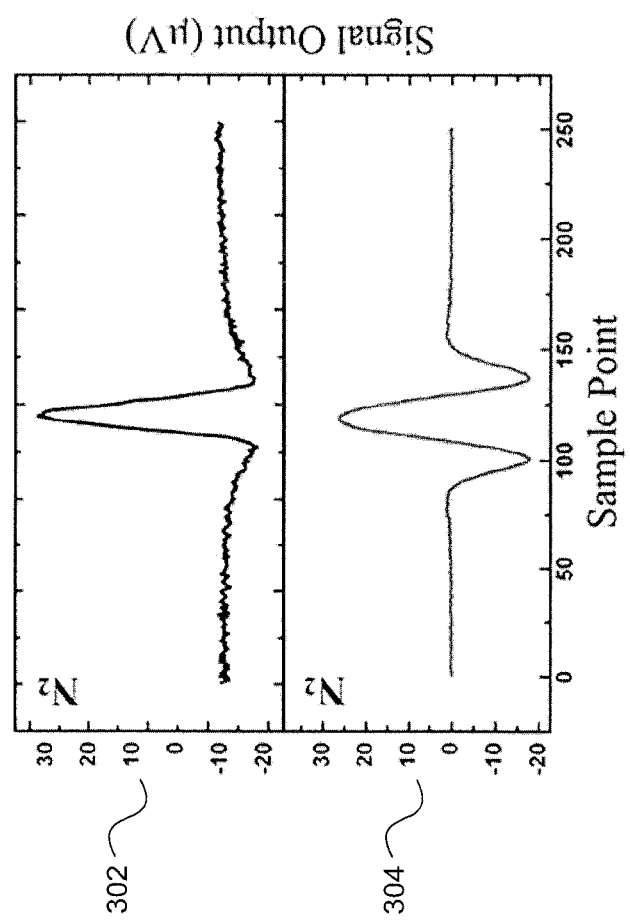

Referring now to FIG. 3, a diagram the spectral response of a single nitrogen gas under two beams having opposite OAM modes, with the first spectrum 302 having an OAM of −3 and the second spectrum 304 having an OAM of +3. Since OAM beams for multiplexing can be regarded as an analog of spatial division multiplexing and mode division multiplexing, each orthogonal spatial mode serves as an independent MIR laser spectroscopic sensor to measure the concentration of gas molecule-se. If two or more different OAM modes are used to do error correction upon a single gas, as in FIG. 3, higher spectral resolution and faster time response can be achieved.

It should be noted that OAM multiplexing can be achieved by tuning the mode order of a ring cavity in OAM converter 104 at a high speed. The OAM beams can be multiplexed using non-polarizing beamsplitting and combined with polarization multiplexing with polarizing beamsplitters, after which the light passes through gas 108 and is attenuated by the energy absorbed by gas molecules. After that, the polarization multiplexed OAM beams are first polarization-demultiplexed by a polarizer and then demultiplexed to individual OAM beams with a planar phase front for coherent detection.

Figure 4:
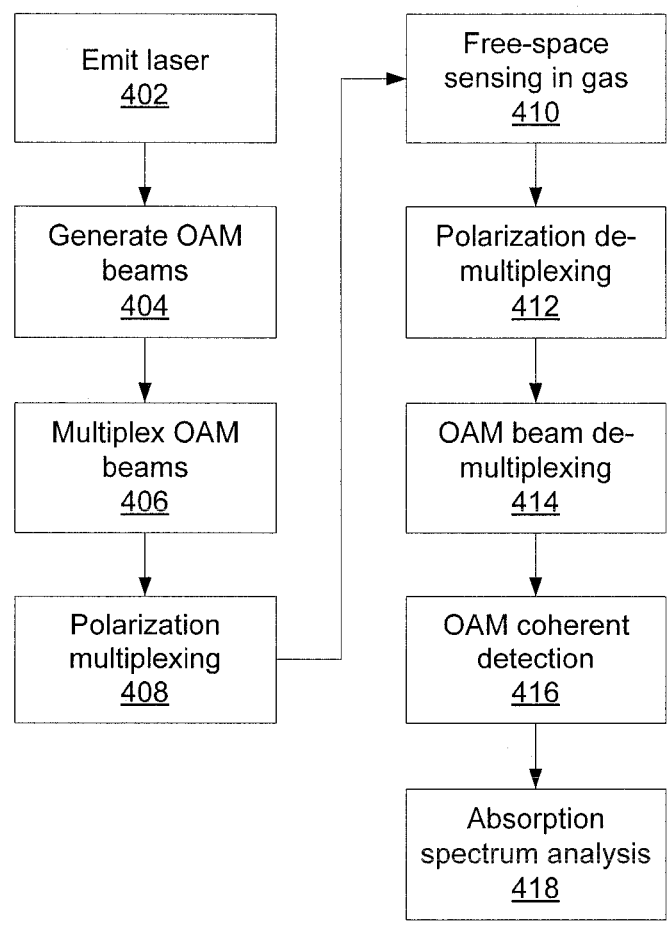
FIG. 4 is a block/flow diagram of a method for orbital angular momentum spectroscopy in accordance with the present principles.

Referring now to FIG. 4, a method of OAM spectroscopy is shown. Block 402 generates and emits a laser using the laser 102. It should be recognized that, while MIR laser light is specifically contemplated herein, the present principles may be applied to any wavelength. Block 404 generates N OAM beams by splitting the emitted laser beam into N separate beams and applying, e.g., free-space mode conversion with phase plates and hologram plates. The N OAM beams are multiplexed in block 406 and subsequently polarization multiplexed in block 408 to provide signals on orthogonal polarizations and at multiple different OAM values. The OAM and polarization multiplexed beams pass through the gas 108 in block 410.

Block 412 performs polarization demultiplexing and block 414 demultiplexes the N OAM beams from the orthogonal polarizations. Block 416 performs coherent detection of the OAM beams, including separate detection of each of the orthogonal polarizations, to convert the output signals into the digital domain. Block 418 then performs absorption spectrum analysis to determine the presence and concentration of trace gases within the gas 108.

Figure 5:
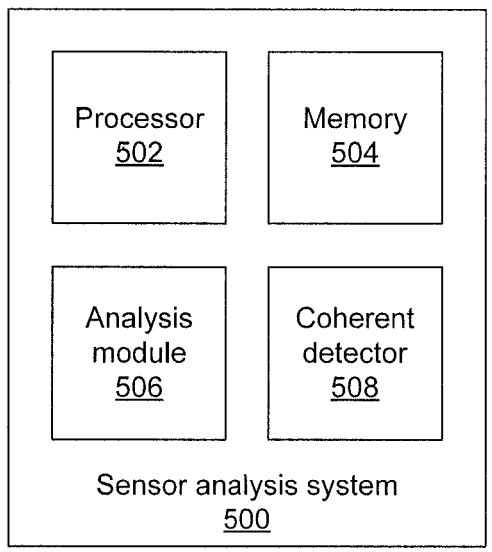
FIG. 5 is a block diagram of a sensor analysis system in accordance with the present principles.

Referring now to FIG. 5, a sensor analysis system 500 is shown that processes the data provided by the sensor 100. The system 500 includes a hardware processor 502 and a memory 504 that stores one or more spectral patterns for respective gases that the sensor 100 is sensitive to. An analysis module 506 uses the processor 502 and the stored spectral patterns to match against spectra detected by the sensor 100 for each of the respective OAM beams. The system 500 may also include a coherent detector to receive the OAM beams directly, providing immediate input from the sensor 100.

Figure 6:
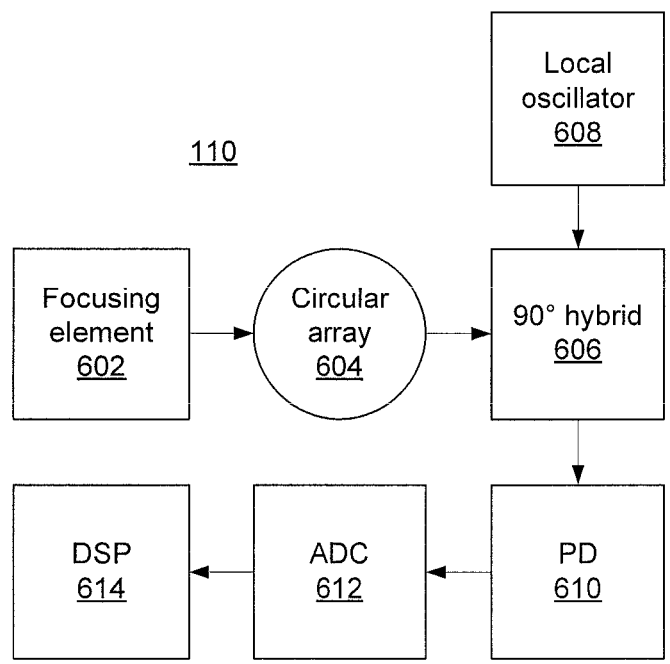
FIG. 6 is a block diagram of an orbital angular momentum receiver in accordance with the present principles.

Referring now to FIG. 6, a block diagram of OAM receivers 106/110 is shown. A focusing element 602 receives the OAM beams from the detector and passes them to a circular array 604. The circular array 604 performs optical demultiplexing using multiple sub-apertures, with each sub-aperture coupled to a single-mode fiber. The outputs of the circular array are coupled with a local oscillator signal 608 and received with a photodetector 610 to convert from the optical to the electrical domain. An analog-to-digital converter 612 converts the analog electrical signals to the digital domain, and the signals are then processed by digital signal processing 614 to extract spectrographic information.

It should be understood that embodiments described herein may be entirely hardware, entirely software or including both hardware and software elements. In a preferred embodiment, the present invention is implemented in hardware and software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention.

The invention claimed is:

1. A method for optical angular momentum (OAM) spectroscopy, comprising:
    generating a plurality of beams of light, each beam having a different respective OAM mode, by splitting a laser beam and imposing a respective OAM mode onto each of the split beams;
    detecting a first absorption spectrum of each of the beams of light;
    passing the beams of light through a gas at the same time to attenuate the beams of light in accordance with a presence and concentration of a respective gas after detecting the first absorption spectra;
    coherently detecting a second absorption spectrum of each of the beams of light; and
    analyzing a difference between the first and second absorption spectra for the beams of light to determine the presence and concentration of the respective gas.

2. The method of claim 1, wherein the laser beam has a wavelength in the middle infrared range.

3. The method of claim 1, wherein imposing an OAM mode on a beam of light comprises passing the beam through a phase plate.

4. The method of claim 1, wherein imposing an OAM mode on a beam of light comprises passing the beam through a hologram plate.

5. The method of claim 1, wherein analyzing the difference between the first and second spectrum comprises matching the difference to an expected spectrum for the respective gas.

6. The method of claim 1, further comprising splitting the beam of light into orthogonal polarizations before the beam passes through the gas.

7. The method of claim 6, wherein coherently detecting the second spectrum comprises independently detecting each of the orthogonal polarizations.

8. An optical angular momentum (OAM) spectroscopy sensor, comprising:
- a laser configured to output a plurality of unconverted beams;
- an OAM converter configured to impose a respective OAM mode on each of the unconverted beams to produce respective OAM beams;
- a first OAM receiver configured to detect a first absorption spectrum of each of the OAM beams from the OAM converter;
- a gas cavity containing a mixture comprising one or more component gases configured to attenuate each of the OAM beams at the same time in accordance with a presence and concentration of a respective gas;
- a second OAM receiver configured to coherently detect a second absorption spectrum of each of the OAM beams after the OAM beams have passed through the gas cavity; and
- a processor configured to analyze a difference between the first and second absorption spectra for the beams of light to determine the presence and concentration of the respective gas.

9. The sensor of claim 8, wherein the laser output has a wavelength in the middle infrared range.

10. The sensor of claim 8, wherein the OAM converter comprises a phase plate to impose an OAM mode on a beam.

11. The sensor of claim 8, wherein the OAM converter comprises a hologram plate to impose an OAM mode on a beam.

12. The sensor of claim 8, wherein the processor is further configured to match the difference to an expected spectrum for the respective gas.

13. The sensor of claim 8, further comprising a polarizing splitter configured to split the OAM beam into orthogonal polarizations before the beam passes through the gas cavity.

14. The sensor of claim 13, wherein the second OAM receiver is configured to independently detect each of the orthogonal polarizations.

* * * * *